US009650659B2

(12) United States Patent
Sim et al.

(10) Patent No.: US 9,650,659 B2
(45) Date of Patent: May 16, 2017

(54) DISCRIMINATION METHOD FOR MUTATION-INDUCED UNICELLULAR ORGANISM AND MICROFLUIDIC DEVICE USED THEREFOR

(71) Applicant: Korea University Research and Business Foundation, Seoul (KR)

(72) Inventors: Sang Jun Sim, Seoul (KR); Young Hwan Kim, Seoul (KR); Ho Seok Kwak, Seoul (KR)

(73) Assignee: KOREA UNIVERSITY RESEARCH AND BUSINESS FOUNDATION, Seoul (KR)

(*) Notice: Subject to any disclaimer, the term of this patent is extended or adjusted under 35 U.S.C. 154(b) by 0 days.

(21) Appl. No.: 14/760,607

(22) PCT Filed: Jan. 14, 2014

(86) PCT No.: PCT/KR2014/000373
§ 371 (c)(1),
(2) Date: Jul. 13, 2015

(87) PCT Pub. No.: WO2014/112762
PCT Pub. Date: Jul. 24, 2014

(65) Prior Publication Data

US 2015/0353981 A1 Dec. 10, 2015

(30) Foreign Application Priority Data

Jan. 21, 2013 (KR) ........................ 10-2013-0006466

(51) Int. Cl.
*C12Q 1/06* (2006.01)
*C12Q 1/02* (2006.01)
(Continued)

(52) U.S. Cl.
CPC ................ *C12Q 1/02* (2013.01); *C12Q 1/04* (2013.01); *B01L 3/5027* (2013.01); *G01N 2035/00158* (2013.01)

(58) Field of Classification Search
CPC ........................................................ C12Q 1/06
See application file for complete search history.

(56) References Cited

U.S. PATENT DOCUMENTS 5,652,098 A 7/1997 Freyer
6,060,046 A * 5/2000 Steinberg ............ C09D 5/1625 424/78.09

(Continued)

OTHER PUBLICATIONS

Kirst, H., et al., "Assembly of the Light-Harvesting Chlorophyll Antenna in the Green Alga Chlamydomonas reinhardtii Requires Expression of the TLA2-CpFTSY Gene", "Plant Physiology", Feb. 2012, pp. 930-945, vol. 158.

(Continued)

*Primary Examiner* — Rosanne Kosson
(74) *Attorney, Agent, or Firm* — Hultquist, PLLC; Steven J. Hultquist

(57) ABSTRACT

The present invention discloses a microfluidic photoreaction system and a method for screening a single cell organism having changed light-response characteristics. According to the present invention, an improved single cell organism can be effectively screened based on phototaxis using a microfluidic system. Specifically, easy monitoring at the cellular level is possible, and a mutant strain having an increased response and/or sensitivity to light can be easily and rapidly screened by various analyses, including statistical analysis of collected results. Thus, the present invention can be effectively used to investigate the correlation between phototaxis and photoconversion efficiency and to screen a single cell organism having increased photosynthetic efficiency.

14 Claims, 15 Drawing Sheets

(51) Int. Cl.

| | |
|---|---|
| ***C12Q 1/04*** | (2006.01) |
| *G01N 35/00* | (2006.01) |
| *B01L 3/00* | (2006.01) |

(56) References Cited

U.S. PATENT DOCUMENTS

| | | | |
|---|---|---|---|
| 2008/0044887 A1 | 2/2008 | Maltezos et al. | |
| 2008/0194029 A1* | 8/2008 | Hegemann | C12N 15/8213 435/468 |
| 2012/0225475 A1 | 9/2012 | Wagner et al. | |
| 2012/0329089 A1 | 12/2012 | Edrei | |

OTHER PUBLICATIONS

Hirschberg, R., et al., “Phototaxis Mutants of Chlamydomonas reinhardtii”, “Journal of Bacteriology”, Feb. 1, 1977, pp. 803-808, vol. 129, No. 2.

Kim, J., et al., “Microfluidic High-Throughput Selection of Microalgal Strains with Superior Photosynthetic Productivity Using Competitive Phototaxis”, “Scientific Reports”, Feb. 8, 2016, pp. 21155-21165, vol. 6.

Pazour, G., et al., “Mutational Analysis of the Phototransduction Pathway of Chlamydomonas reinhardtii”, “The Journal of Cell Biology”, Oct. 15, 1995, pp. 427-440, vol. 131, No. 2, Publisher: The Rockefeller University Press.

Takahashi, T., et al., “Diversion of the Sign of Phototaxis in a Chlamydomonas reinhardtii Mutant Incorporated with Retinal and its Analogs”, “Federation of European Biochemical Studies”, Dec. 1, 1992, pp. 275-279, vol. 314, No. 3.

Weibel, D., et al., “Microoxen: Microorganisms to Move Microscale Loads”, “Proceedings of the National Academy of Sciences”, Aug. 23, 2005, pp. 11963-11967, vol. 102, No. 34.

Amano, M., et al., “Photosynthesis affects the sign of phototaxis of Chlamydomonas reinhardtiimutants”, “Biophysics”, Aug. 1995, vol. 35, No. Supplement, p. S38. col. [1E03].

Amano, M., et al., “Photosynthesis affects the sign of phototaxis of Chlamydomonas reinhardtiimutants”, “Biophysics”, Aug. 1995, vol. 35, No. Supplement, p. S38. col. [1E03]; (English Translation).

* cited by examiner

DISCRIMINATION METHOD FOR MUTATION-INDUCED UNICELLULAR ORGANISM AND MICROFLUIDIC DEVICE USED THEREFOR

CROSS-REFERENCE TO RELATED APPLICATIONS

This application is a U.S. national phase under the provisions of 35 U.S.C. §371 of International Patent Application No. PCT/KR14/00373 filed Jan. 14, 2014, which in turn claims priority of Korean Patent Application No. 10-2013-0006466 filed Jan. 21, 2013. The disclosures of such international patent application and Korean priority patent application are hereby incorporated herein by reference in their respective entireties, for all purposes.

TECHNICAL FIELD

The present invention relates to a method for screening a single cell organism with mutation and a microfluidic system for use in the method, and more particularly, to a method of screening a single cell organisms with mutation based on phototaxis, the method comprising the steps of: irradiating a population of single cell organism with light to induce phototaxis; calculating the phototactic indices of the single cell organisms; and selecting the single cell organism as desired single cell organism with mutation, if the phototactic indices of the single cell organisms differ from those of a control group.

BACKGROUND ART

Various single cell organisms, including bacteria, yeasts and microalgae, are used for various purposes in the agricultural, livestock farming, marine fisheries, medicinal and resources fields. For example, bacteria and yeasts are widely used for the expression of medicinal proteins. Particularly, microalgae have the capability to produce a large amount of neutral lipids, which can be converted to biodiesel, from photoenergy, carbon dioxide and inorganic materials, and thus have recently received attention as an alternative that can solve the energy resources exhaustion problem resulting from a rapid increase in the use of fossil fuels and the global warming problem resulting from greenhouse gas emissions.

Microalgae contain pigments such as chlorophyll, carotinoids and phycobilins, and are single cell algae that can grow through photosynthesis and can synthesize organic materials required for photosynthesis. Most phytoplanktons belong to microalgae. It has been reported to date that more than hundreds of thousands of species of microalgae are present in freshwater and marine ecosystems, and research and development has been performed for various purposes. Due to limitations on genetic manipulation, there is much difficulty in improving strains to increase productivity.

For the efficient use of such microalgae, the development of an optimal strain suitable for purposes, the optimization of media, the design of an optimal reactor, studies on metabolic processes and product purification, etc., are required.

One of methods for developing an optimal strain comprises inducing specific or random mutation in the genome of microalgae, and identifying a strain showing desired properties, for example, increased photosynthetic efficiency, high lipid production or rapid growth rate.

U.S. Patent Publication No. 2008-00254493 is directed to a method for screening a mutant microbial strain that does not express protease, and discloses a method comprising culturing mutation-induced strains on a gel containing a protease substrate, and identifying a mutant strain based on whether the substrate was degraded.

Korean Patent Laid-Open Publication No. 2011-0018798 is directed to a microfluidic cell chip, a method of quantitatively analyzing cell death using the same, and a system of analyzing a cell image using the same, and discloses a system and method capable of analyzing and imaging cell death in real time using a microfluidic system.

However, in many cases, it is required to perform screening of tens of thousands of strains, which requires complex biochemical and molecular biological analysis. Thus, it is required to develop a method capable of high-throughput screening of strains in the initial stage of screening.

Accordingly, the present inventors have made extensive efforts to solve the above-described problem and develop a method for efficiently screening single cell organisms, and as a result, have found that improved single cell organisms can be effectively screened using a microfluidic photoreaction system based on phototaxis, thereby completing the present invention.

SUMMARY OF THE INVENTION

It is an object of the present invention to provide a method and system for rapid and efficient screening the single cell mutant organisms having characteristics such as an increased response to light.

To achieve the above object, the present invention provides a method of screening a single cell organism with mutation based on phototaxis, the method comprising the steps of: (a) irradiating a population of single cell organism with light to induce phototaxis; (b) calculating the phototactic indices of the single cell organisms; and (c) selecting the single cell organism as desired single cell organism with mutation, if the phototactic indices of the single cell organisms differ from those of a control group.

The present invention also provides a single cell organism with mutation screened by the above-described method.

The present invention also provides a microfluidic photoreaction system for analysis of phototactic response of the single cell organism comprising: a light-transmitting, individual inlet unit; an individual reaching unit formed separately from the individual inlet unit; a channel unit connected to the individual inlet unit and the individual reaching unit; and a measuring unit formed between both ends of the channel unit.

DETAILED DESCRIPTION OF THE INVENTION

Figure 1:
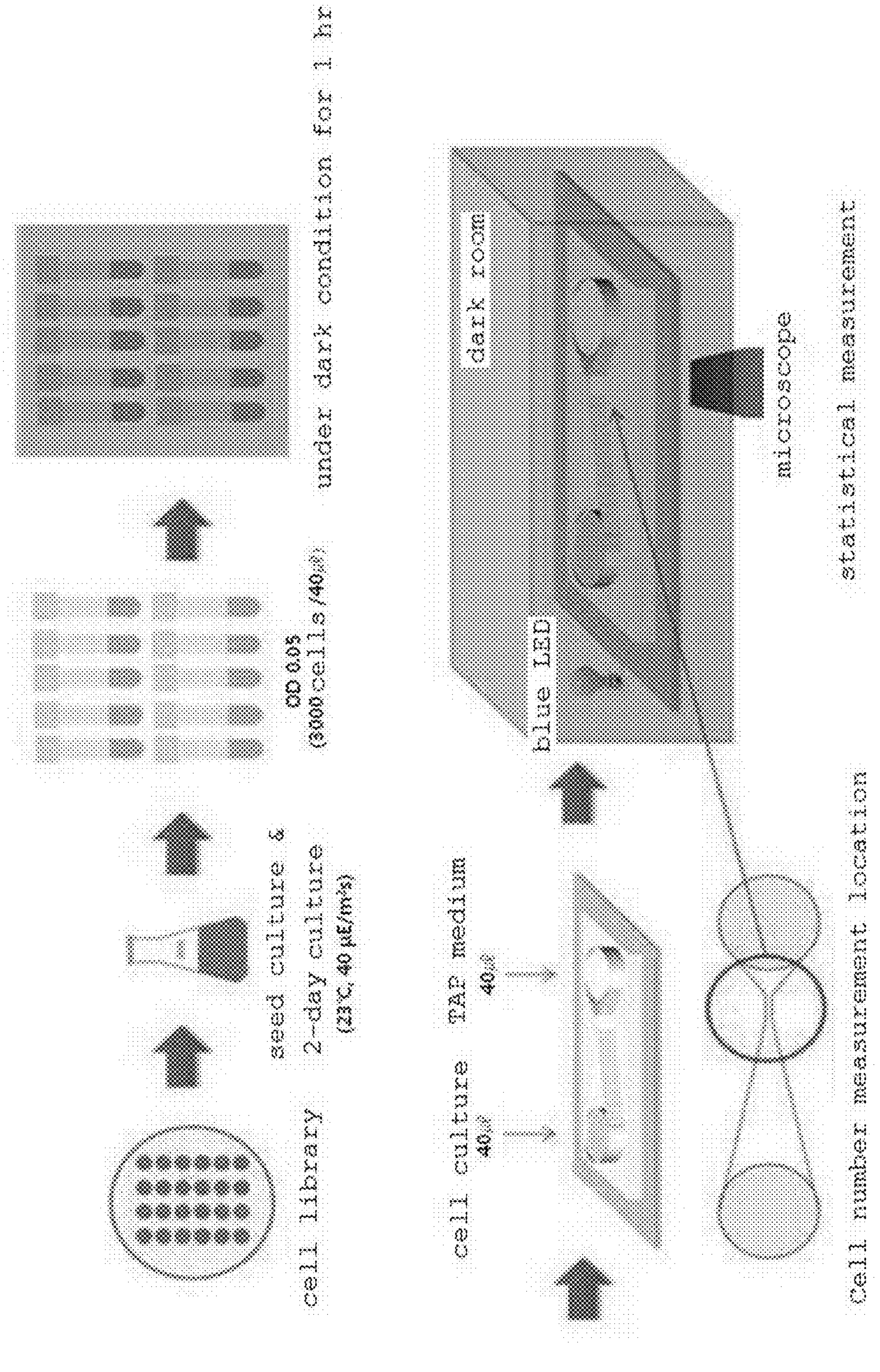
FIG. 1 is a schematic diagram showing an overall process of phototaxis-based screening method for selecting the strains showing a sensitive response to the light in microfluidic system according to an embodiment of the present invention.

Unless defined otherwise, all technical and scientific terms used herein have the same meaning as commonly understood by one of ordinary skill in the art to which the invention pertains. Generally, the nomenclature used herein are well known and are commonly employed in the art.

The present invention is based on the finding that a mutant having an increased response to the light can be effectively screened from motile photosynthetic single cell organisms based on a difference in phototaxis. Specifically, according to the present invention, it has been found that a mutant strain having a specific response to light can be rapidly and efficiently screened by statistically analyzing the motility of mutant cells in a microfluidic system based on a difference in the sensitivity and/or response of single cell organisms to light.

Thus, in one aspect, the present invention is directed to a method of screening a single cell organism with mutation based on phototaxis, the method comprising the steps of: (a) irradiating a population of single cell organism with light to induce phototaxis; (b) calculating the phototactic indices of the single cell organisms; and (c) selecting the single cell organism as desired single cell organism with mutation, if the phototactic indices of the single cell organisms differ from those of a control group.

As used herein, the term "single cell organisms" is used interchangeably with the term "cells" or "strains", and refers to various single cell organisms that are motile and show a response to light and phototaxis. The term is intended to include, for example, photosynthetic bacteria or bacteria, protozoans such as photosynthetic Euglena, or microalgae. In an embodiment of the present invention, the microalga *Chlamydomonas reinhardtii* is typically used.

As used herein, the term "phototaxis" refers to the movement of a single cell organism in response to light, and is intended to include both positive phototaxis toward the light and negative phototaxis away from the light. Although a single cell organism shows positive phototaxis at a certain intensity of light, it may show negative phototaxis when the intensity of light is higher than a certain level.

As used herein, the term "mutation" refers to a mutation that occurs at the genetic level to cause a difference in phenotypes, particularly phototaxis, light response and/or light sensitivity, compared to a wild-type control. The term is intended to include not only naturally occurring mutations, but also artificially introduced mutations. Mutations include random or site-specific mutations, and mutations caused by the addition, deletion and/or replacement of nucleotides in a gene.

As used herein, the term "desired mutant" or "having desired characteristics" or "mutant having desired characteristics" means that one or more characteristics to be improved in a single cell organism is changed, for example, improved or enhanced, due to the above-described genetic change. The term may include various characteristics depending on the intended use of a single cell organism. For example, if a microalga is used as a single cell organism, the characteristics include photosynthesis-related characteristics or indices, for example, changes in photosynthetic mechanisms including photosynthetic pigments, photosynthesis efficiency and photoconversion efficiency, and may also include changes in growth rate, lipid contents and lipid components, but are not limited thereto. To determine the degree of improvement, the corresponding characteristic of the single cell organism with mutation can be compared with that of a control. Any person skilled in the art can select a suitable standard in view of an improved characteristic. For example, a single cell organism showing an improvement of about 5% or more, about 10% or more, about 20% or more, about 30% or more, about 40% or more, about 50% or more, about 60% or more, about 70% or more, about 80% or more, about 90% or more, or about 100% or more compared to a control, can be selected as a desired single cell organism with mutation.

Single cell organisms that are used in the inventive method for screening mutant individuals showing improved characteristics may be derived from a mutant library including various single cell organisms anticipated to have one or more natural or artificial mutations in the genome. In addition, single cell organisms that are used in the inventive method may be derived either from single colonies derived from single cells anticipated to include a kind of mutation, or from multiple colonies derived from multiple cells including one or more same or different mutations. For example, single colony may be used to screen single cell organism with mutation showing optimal characteristics by analyzing characteristics or the individual characteristics of single colonies. In addition, a mixture of multiple colonies may be used to efficiently screen genetically mutated desired organisms having desired characteristics from a mutant library.

The method of the present invention can be effectively used to screen a desired mutant individual either from naturally occurring mutants or several to tens of thousands of mutants included in artificial mutant library by a rapid and simple analysis method based on phototaxis. Particularly, in the case of the latter, a large amount of single cell organism with mutation can be rapidly and efficiently screened by repeatedly performing the method of the present invention.

As used herein, the term “light response” means that the characteristic of single cell organisms that move away from a light source by phototaxis when they are irradiated with light. The light response may be measured as the number of cells that reached to the side opposite the light source by phototaxis, among total cells introduced, for example, about 3,000 cells, when light having a certain intensity, for example, 30 μmol photon $m^{-2}s^{-1}$, is irradiated for a certain time, for example, 30 minutes.

As used herein, the term “light sensitivity” means the characteristic of single cell organisms that rapidly move to the side opposite a light source when they are irradiated with light. The light sensitivity can be measured as the time taken for the single cell organism to move a certain distance, for example, 3 cm, by phototaxis, when the single cell organism is irradiated with light having a certain intensity, for example, 30 μmol photon $m^{-2}s^{-1}$.

The method according to the present invention is based on the response of a single cell organism to light. The phototactic response indices or phototactic indices used in the present invention are indices that can indicate a change in the characteristic of a single cell organism that responded to light, and it may include various values. The phototactic indices can be calculated through the measurement of at least one of the light response and the light sensitivity. Such phototactic indices include all those that can measure changes related to a response to light in comparison with a control. Specifically, the phototactic indices used in the method of the present invention include: (i) the ratio of the number of single cell organisms that moved per unit time in response to light to the total number of single cell organisms; (ii) histogram peak analysis based on the distribution of single cell organisms that moved per unit time; and (iii) the average time taken for single cell organisms to move a unit distance, the speed of the movement, or the variation thereof. For example, the phototactic indices can be calculated by various methods as described in the Examples of the present invention and as shown in FIGS. 3 to 9. For example, the shift of the peak of the reaching time of a wild type strain and a mutant strain can be observed by peak analysis as shown in FIG. 5, and the maximum response time and the percentage of cells that responded to light can be analyzed by peak analysis.

When the method of the present invention is used in the inventive system as described below, the phototactic indices include, but are not limited to: (i) the ratio of the number of cells, which moved to the reaching unit through the channel for a certain time, to the total number of cells used; (ii) the average time taken for a certain number of cells to move to the reaching unit, or the variation thereof; (iii) the speed at which the cells used in the method move to the reaching unit; and (iv) the distribution of cell number as a function of the time taken for the cells used in the method to move to the reaching unit.

Single cell organisms that may be used in the method of the present invention are as mentioned above. For example, photosynthetic single cell organisms showing phototaxis and motility, and preferably microalgae, are used. In an embodiment, microalgae may be green algae, diatoms, red algae, flagellates, light green algae, brown flagellates, yellow-green algae, dinoflagellates, or blue-green algae. Examples of microalgae include, but are not limited to, green algae (*Chlorella, Dunaliella, Scenedesmus, Haematococcus, Nannochloris*, etc.), diatoms (*Skeletonema, Thalassiosira, Phaeodactylum, Chaetoceros,* etc.), red algae (*Porphyridium cruentum, Galdieria*, etc.), flagellates (*Isochrysis, Pavlova*, etc.), light green algae (*Tetraselmis, Pyramimonas*), brown flagellates (*Chlamydomonas, Rhodomonas, Chroomonas*, etc.), yellow-green algae (*Olistodiscus,* etc.), dinoflagellates (*Crypthecodinium, Alexandrium, Gymnodinium, Chattonella, Karenia*, etc.), and blue-green algae (*Spirulina, Synechococcus, Synechocystis, Cyanidium*, etc.). In an embodiment, brown flagellates are used. Preferably, *Chlamydomonas* spp., *Rhodomonas* spp. or *Chroomonas* spp. is used. More preferably, *Chlamydomonas reinhardtii* is used, but is not limited thereto.

The method of the present invention may further comprise a pretreatment step in which the single cell organism is cultured under a continuous light condition, and then cultured under a dark condition. The pretreatment step is performed in order to culture cells under a continuous light condition to thereby maintain the cells in the exponential phase in which the cells have the highest activity. Culture of the cells under a dark condition immediately before the measurement of phototaxis is performed in order to increase the sensitivity of the cells to light to thereby increase the phototactic response of the cells.

Specifically, the continuous light condition in the pretreatment step is sufficient as long as it is a quality of light by which microalgae that grow by photosynthesis can reach the exponential phase in which the microalgae have the highest activity. In addition, light can be continuously irradiated so that the exponential phase can be more rapidly reached. The light quality and the irradiation time, which satisfy such conditions, are not specifically limited. For example, the continuous light condition is achieved by irradiating light having an intensity of 20-50 μmol photon $m^{-2}s^{-1}$, and preferably about 40 μmol photon $m^{-2}s^{-1}$, for about 12-24 hours, but is not limited thereto.

Varying light intensities and irradiation times may be used as long as the above purpose is achieved. The wavelength used may vary depending on the kind of single cell organisms used. Single cell organisms efficiently sense light at a specific wavelength, and any person skilled in the art can select a suitable wavelength in view of these particulars. For example, the microalga *Chlamydomonas* has an eyespot that is a light sensing portion, and this portion generally senses light at a wavelength of 540-600 nm or 430-500 nm. Thus, light having a wavelength in this range is preferably used.

In addition, the cells are cultured to the exponential phase of the cell growth cycle in the pretreatment step, and then used in a subsequent step. The growth of single cell organism is largely divided into the lag phase (induction phase), the exponential phase (log phase or growth phase), the stationary phase, and the death phase, and any person skilled in the art can discriminate the exponential phase.

Phototaxis in the method of the present invention includes both positive phototaxis and negative phototaxis. Phototaxis is as described above, and in an embodiment of the present invention, negative phototaxis is induced. A strong intensity of light should be irradiated to induce negative phototaxis in single cell organisms that induce positive phototaxis at a general intensity of light. In other words, the intensity of light that can induce negative phototaxis can vary depending on the kind of target organism, and various intensities of light that can achieve this effect can be used. Any person skilled in the art can select a suitable intensity of light based on the degree of phototaxis. In an embodiment of the present invention, microalgae, particularly *Chlamydomonas reinhardtii*, are used, and in this case, the intensity of light may be about 30 μmol photon $m^{-2}s^{-1}cm^{-1}$, but is not limited thereto. The wavelength of light is as mentioned above.

Single cell organisms screened according to the method of the present invention show an increased light response or light sensitivity compared to a control, that is, a wild-type strain, or a comparative strain used as a reference. The change in this characteristic can be measured as the phototactic indices as described above, and single cell organisms having increased phototactic indices can be selected as a desired mutant strain. The degree of improvement in the phototactic indices can vary depending on the kind of single cell organism or index. For example, a single cell organism showing an improvement of about 5% or more, about 10% or more, about 20% or more, about 30% or higher, about 40% or more, about 50% or more, about 60% or more, about 70% or more, about 80% or more, about 90% or more, or about 100% or more compared to a control, can be selected as a desired single cell organism with mutation.

The method of the present invention may comprise an additional step depending on the purpose of constructing a mutant strain. For example, if the screening of a mutant is performed in order to improve photosynthetic characteristics, lipid production or growth rate, the method comprises an additional step of analyzing each characteristic. For example, the method may an additional step of analyzing photosynthetic indices, preferably a change in photosynthetic mechanisms including photosynthetic pigments, photosynthetic efficiency or photoconversion efficiency, but is not limited thereto. This analysis method is known in the art, and any person skilled in the art can select a suitable analysis method. For example, the photosynthetic indices include, but are not limited to, various indices described in the Examples of the present invention and FIGS. 3 to 9, for example, NPQ (non-photochemical quenching), qP (photochemical quenching), and/or chlorophyll a/b ratio.

In another aspect, the present invention is directed to a single cell organism with mutation screened by the method of screening single cell mutant organism based on phototaxis.

The strain may be used for the production of useful substances in various fields according to the form of mutation. For example, *Chlamydomonas reinhardtii* is a species has been most well studied among microalgae, and is easily genetically manipulated (e.g., transformed) compared to other species. In addition, relevant tools have been developed, and the genome sequence of the species was found. Thus, the species is considered as a model organism of microalgae. Accordingly, a mutant strain having an improved photosynthetic mechanism can be screened and used in studies on lipids for biodiesel production, studies on hydrogen production, etc.

Figure 8A:
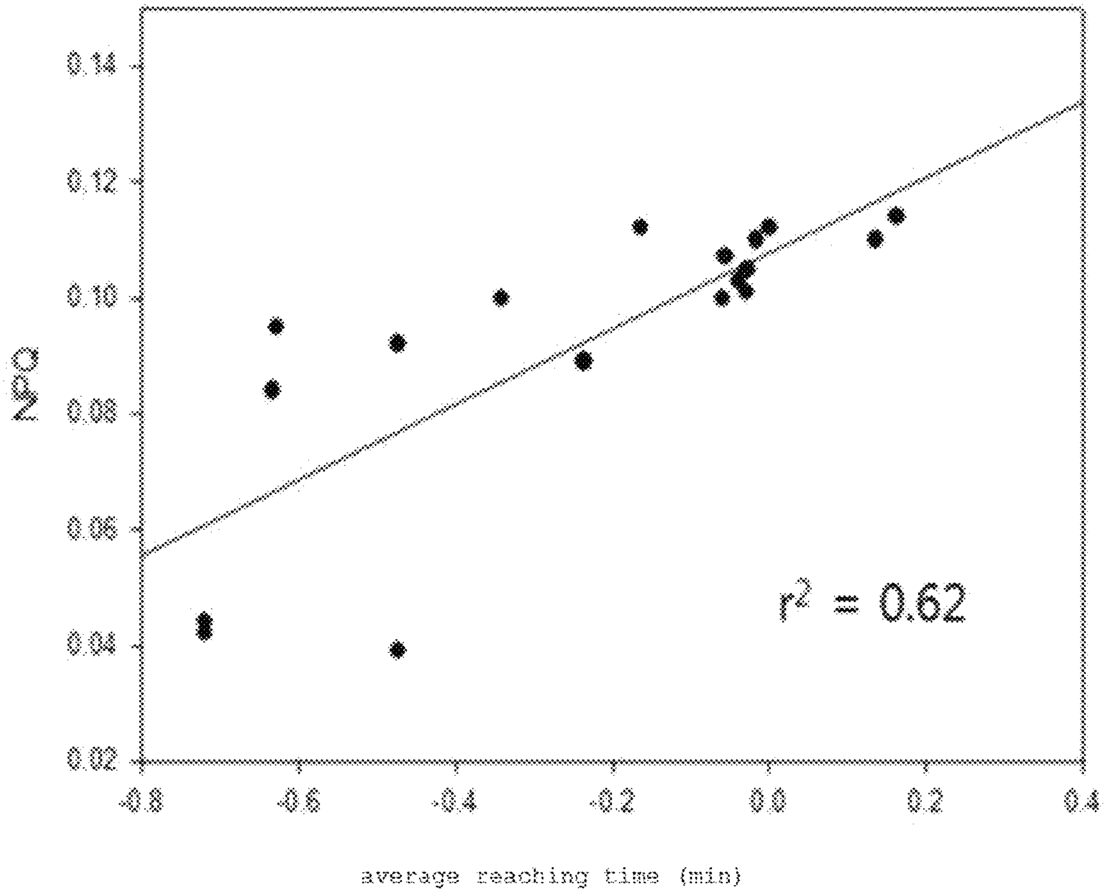
FIG. 8*a* is a graph showing the correlation between the average reaching time that is a phototactic index and NPQ that is an index for measuring photosynthetic efficiency, measured in an embodiment of the present invention. The average reaching time of the mutant strain, which was shortened by phototaxis, showed a low correlation with NPQ that is an index for measuring photosynthetic efficiency, indicating that a strain having increased light sensitivity has high photosynthetic efficiency.
Figure 8B:
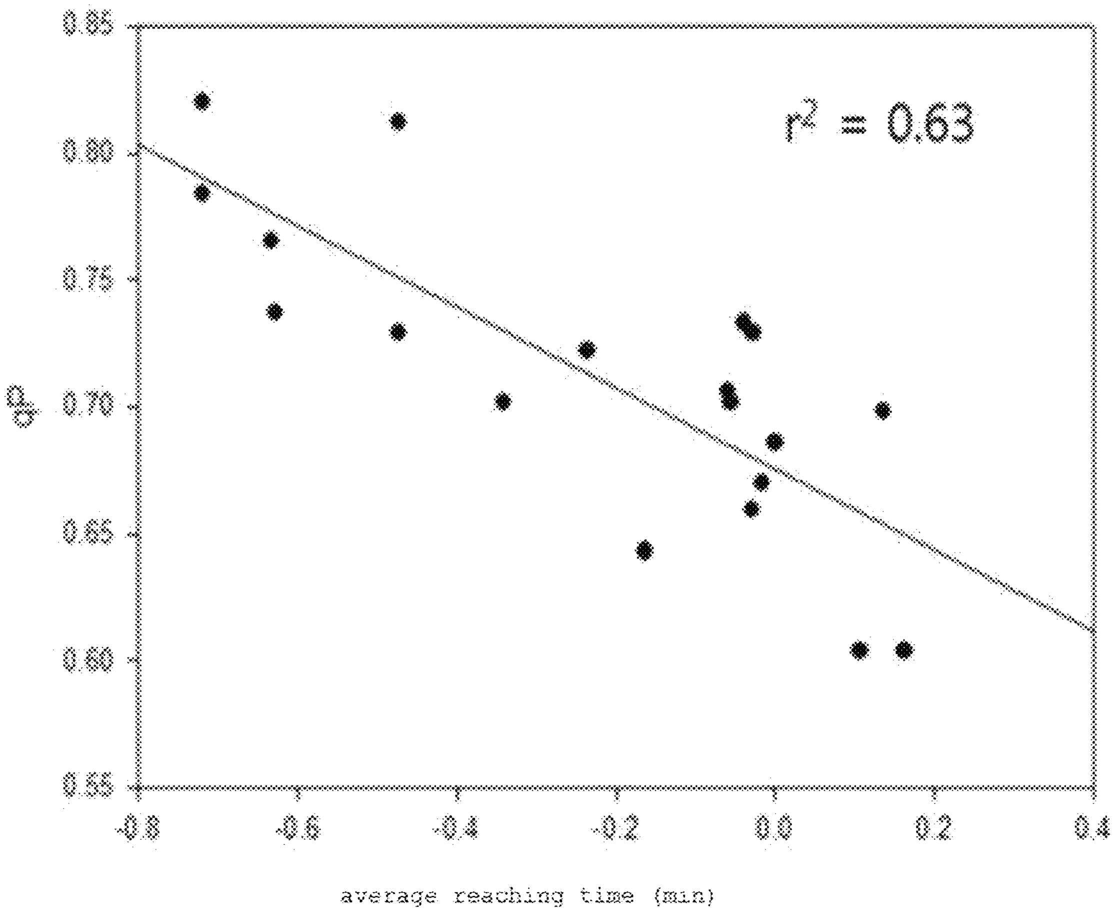
FIG. 8*b* is a graph showing the correlation between the average reaching time that is a phototactic index and qP that is an index for measuring photosynthetic efficiency, measured in an embodiment of the present invention. The average reaching time of the mutant strain, which was shortened by phototaxis, showed a high correlation with the qP that is an index for measuring photosynthetic efficiency, indicating that a strain having increased light sensitivity has high photosynthetic efficiency, like the case of NPQ.
Figure 9:
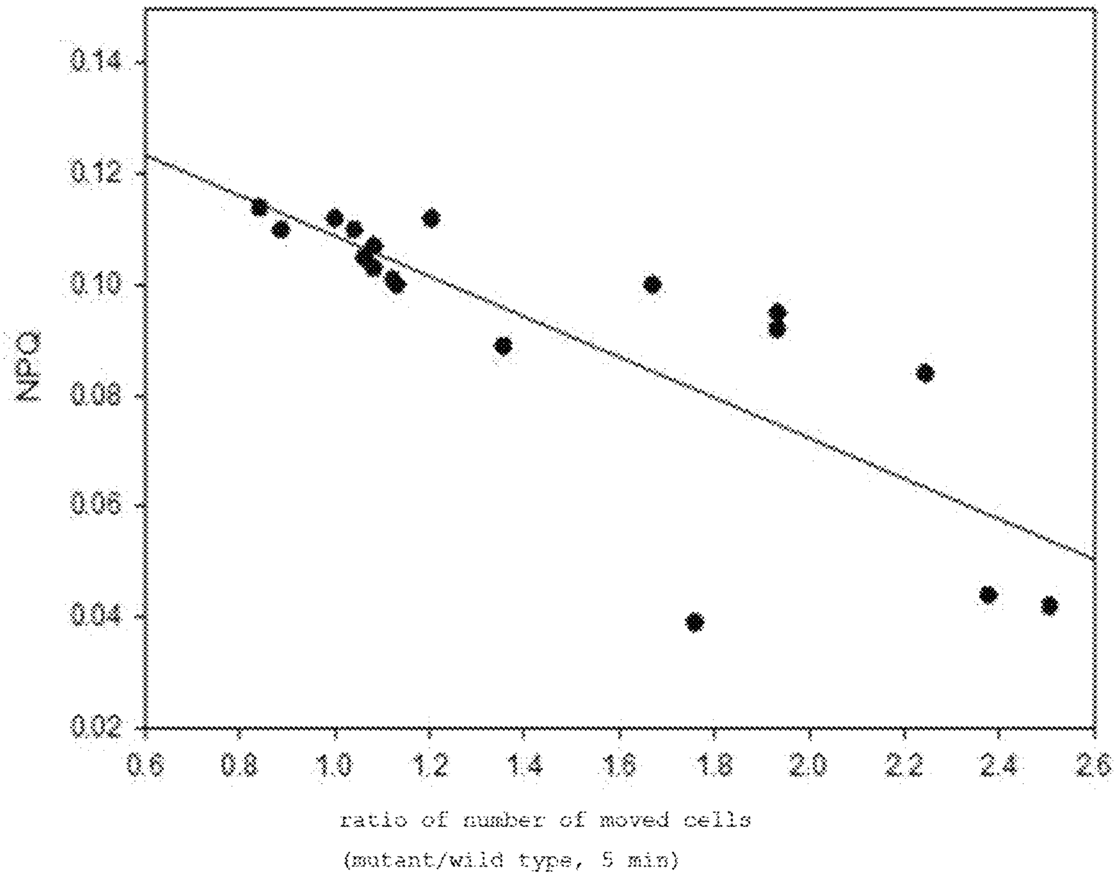
FIG. 9 is a graph showing the correlation between the ratio of the number of cells, which moved a certain distance (3 cm) for a certain time (5 minutes) by phototaxis, to the number of moved cells of a control strain, and NPQ. When the ratio of the number of moved cells in a mutant strain to that in the control strain was 1 or more, a larger number of cells in the mutant strain compared to that in the wild type strain moved. This suggests that the mutant strain has a high response and sensitivity to light. The ratio of the number of moved cells in this mutant strain showed a low correlation with the NPQ value, indicating that this strain has increased photosynthetic efficiency.

As described in the Examples and shown in FIGS. 7 to 9, the strain screened according to the method of the present invention is a desired mutant as demonstrated by analysis of the correlation between the chlorophyll a/b ratio and each of NPQ and qP that are indices for measuring photosynthetic efficiency. This indicates the superiority of the method of the present invention.

In another aspect, the present invention is directed to a microfluidic photoreaction system comprising: a light-transmitting, individual inlet unit; an individual reaching unit formed separately from the individual inlet unit; a channel unit connected to the individual inlet unit and the individual reaching unit; and a measuring unit formed between both ends of the channel unit.

It will be obvious to those skilled in the art that the method of the present invention can be used in various systems, as long as it achieves the purpose of the present invention. In order words, the method of the present invention may be used not only in the system of the present invention, but also in other systems capable of achieving this purpose and having a portion corresponding to each element of the system of the present invention. Hereinafter, the elements included in the system of the present invention and the names thereof will be described by way of example, but the scope of the present invention is not limited thereto, and elements corresponding to the elements of the present invention should be taken into consideration in understanding and interpreting the present invention.

Figure 2A:
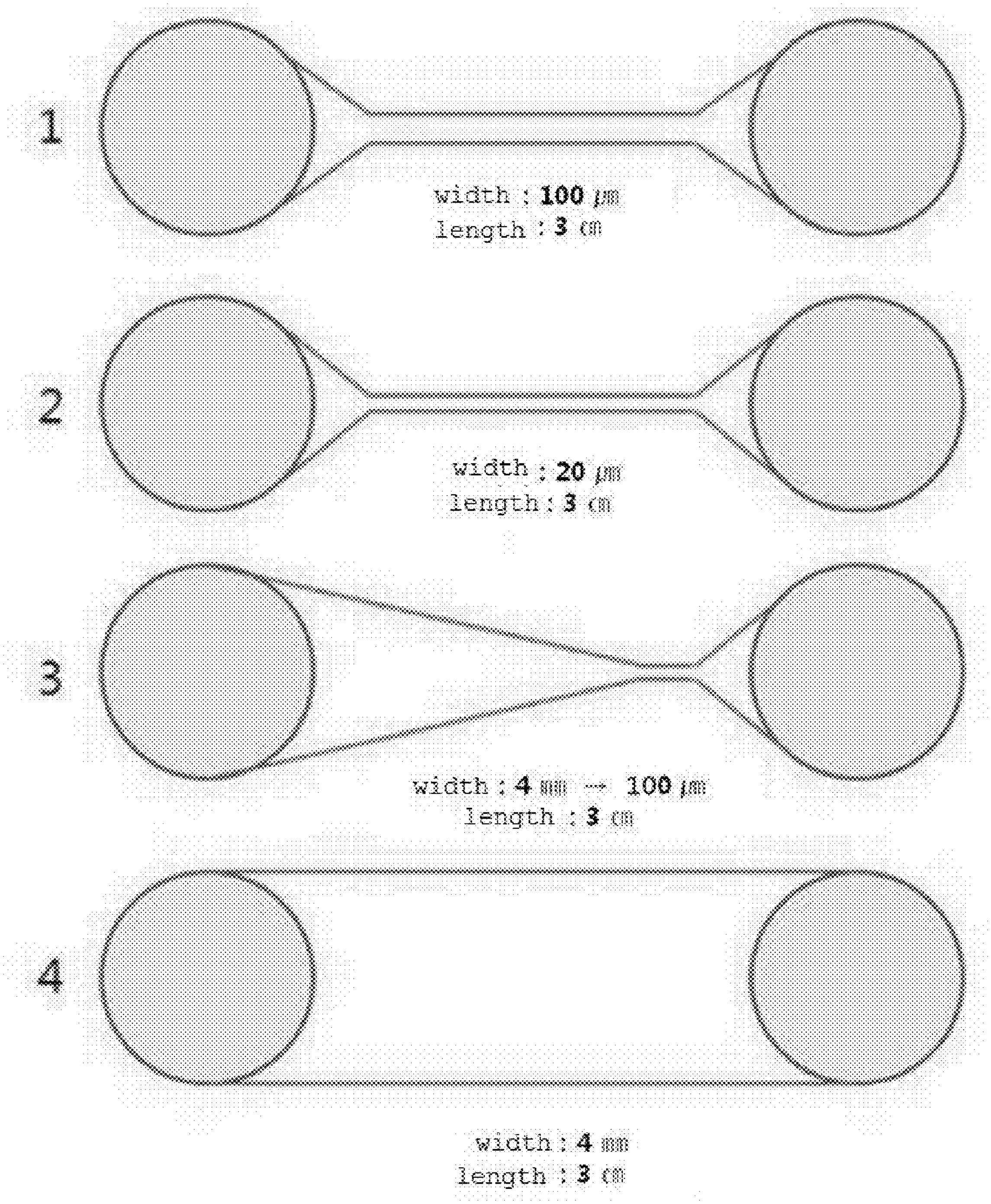
FIG. 2*a* shows the different top views of a phototaxis-based high-throughput screening system that can be used in the present invention.
Figure 2B:
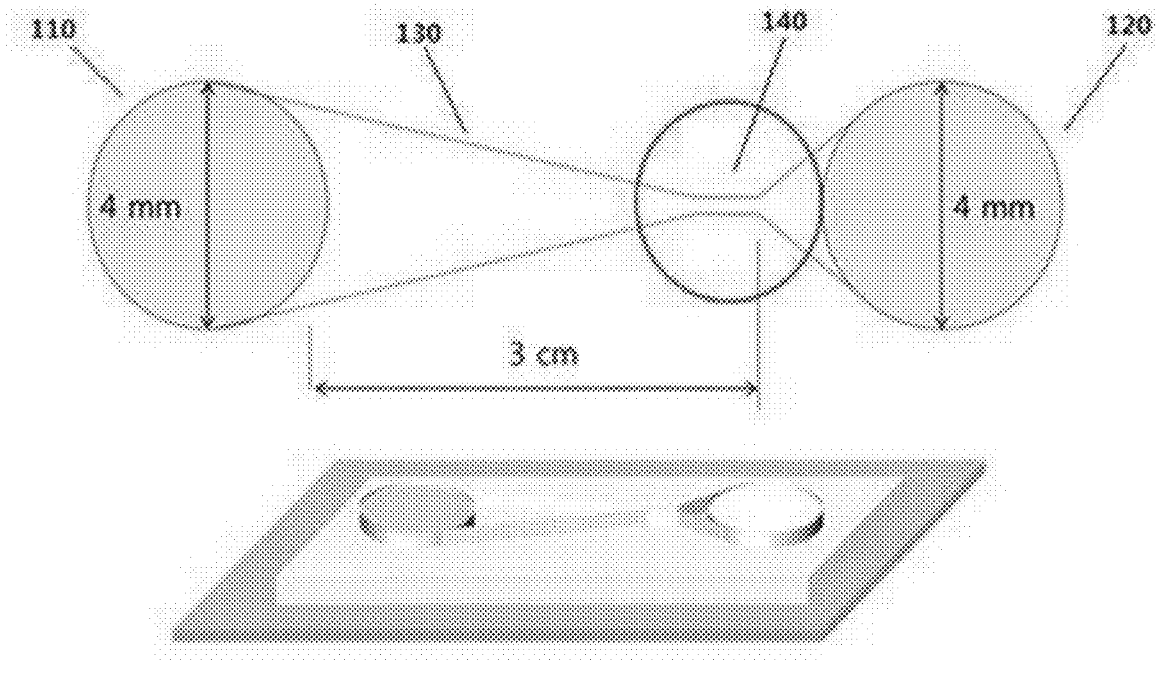
FIG. 2*b* shows a top view (top) and perspective view (bottom) of a phototaxis-based high-throughput screening system used in an embodiment of the present invention.

Referring to FIGS. 2*a* and 2*b*, the system of the present invention comprises an individual inlet unit 110, an individual reaching unit 120 disposed at a predetermined distance from the individual inlet unit 110, and a channel 130 placed between the individual inlet unit 110 and the individual reaching unit 120 and having a shape selected from various shapes. The individual inlet unit 110 and the individual reaching unit 120 may be formed to have a space, a shape and a size so that single cell organisms to be analyzed can be placed therein. In addition, these units may be formed to have various shapes, size and/or materials depending on the size, characteristic and number of individuals to be analyzed, for example, single cell organisms. In an embodiment, these units are made of a light-transmitting material in order to see a response to light. The shapes and sizes of these units are not specifically limited, and these units may have the same or different shapes and sizes.

The channel is formed so that it can fluidically communicate with the individual inlet unit and the individual reaching unit. Through the channel, single cell organisms introduced into the individual inlet unit move together with medium. Thus, the channel is constructed to have a structure and size capable of minimizing resistance so that it does not interfere with the movement of single cell organisms. In an embodiment, the channel is formed to have a diameter equal to or smaller than that of the individual inlet unit or reaching unit. In another embodiment, the channel may have a size as shown in FIG. 2*b*, but the size shown in FIG. 2*b* is illustrative and not restrictive.

Figure 10:
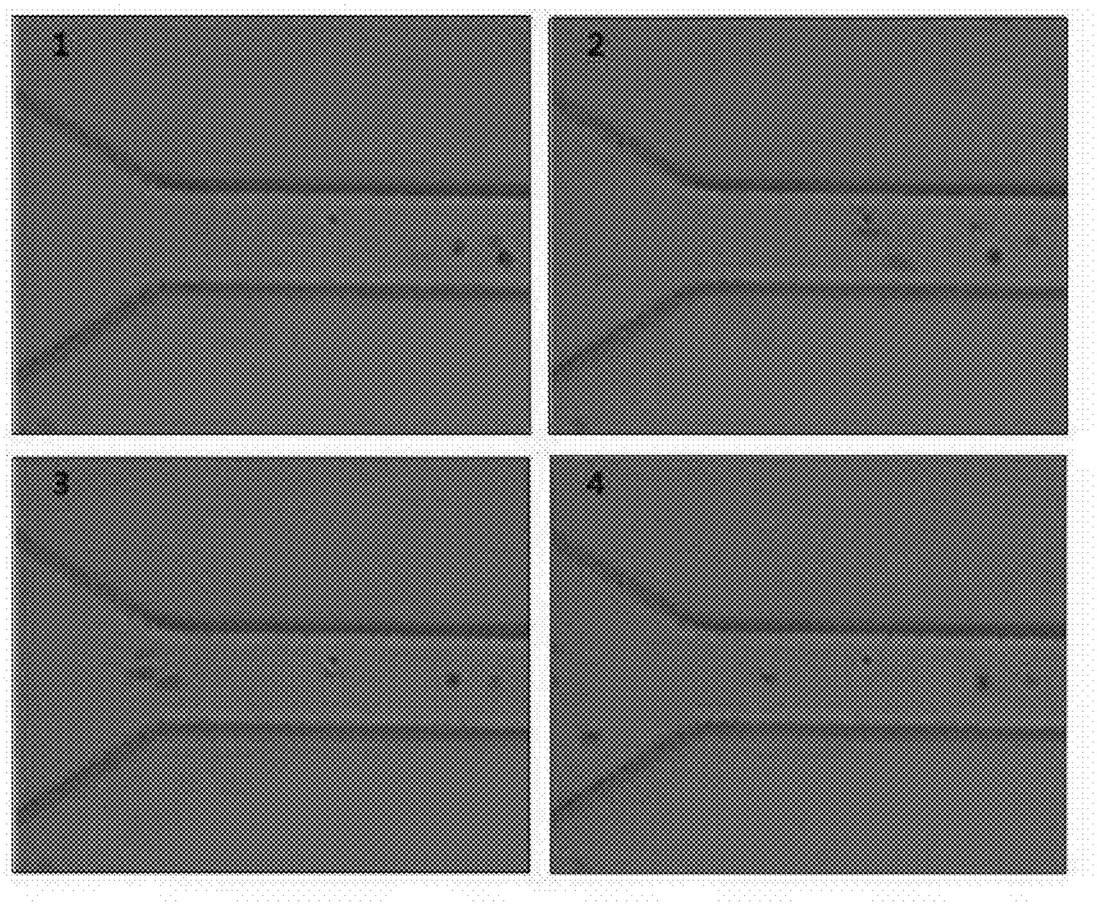
FIG. 10 depicts optical microscope images (×40) showing the actual movement of microalgae by phototaxis in a microfluidic photoreaction system according to an embodiment of the present invention.

Between both ends of the channel, a measuring portion 140 is formed. Referring to FIG. 10, the measuring unit is a portion configured to observe moving single cell organisms at the single cell level by a microscopic method. The measuring unit is formed to have a structure and size that enables the movement of single cell organisms to be individually observed. For example, the measuring unit may be formed to have such a size that about 1 to 5 cells can pass through the measuring unit, based on the diameter of cells to be used in the system of the present invention. The size of the measuring unit may vary depending on the specific size of single cell organisms used. For example, the diameter of the measuring unit may be 10-200 μm. Particularly, if the microalga *Chlamydomonas* is used, the diameter of the measuring unit may be about 50-100 μm, but is not limited thereto.

Each of the elements included in the microfluidic photoreaction system of the present invention is preferably made of a light-transmitting transparent material. This light-transmitting material is not toxic, is porous so that a substance required for bioactivity is easily transferred, and is a material that does not interfere with the movement of single cell organisms or is a material pretreated so as to have these characteristics. Examples of this material include, but are not limited to, PMMA (poly(methyl methacrylate)), PS (polystyrene) and PDMS (polydimethylsiloxane).

Referring to FIG. 1, the microfluidic photoreaction system of the present invention may further comprise a light source. A light source and wavelength that can induce desired optimal phototaxis in single cell organisms used in the system of the present invention, and various light sources and light wavelengths may be used depending on organisms to be analyzed and purposes, as long as these exhibit this effect.

The light source may be any light source that can emit light at a certain wavelength. For example, it may be a laser diode or a light emitting diode (LED). In an embodiment of the present invention, LED light sources that emit green and blue wavelengths are used when microalgae, particularly *Chlamydomonas reinhardtii,* are used as single cell organisms to be analyzed.

FIG. 1 is a schematic view illustrating the system of the present invention and a method of screening single cell mutant organisms (i.e., strain) using the system. The microfluidic photoreaction system according to the present invention may be used to screen organisms having changed light response characteristics, based on the phototaxis of motile single cell organisms. For example, when a certain amount of phototactic or motile single cell organisms (e.g., microalgae) derived from single or multiple colonies are introduced into the cell inlet unit of the system of the present invention, and then irradiated with strong light having a specific intensity, the cells move through the channel in response to the light in a direction away from the light source. When the cells that moves through the channel pass through the measuring unit, various data for calculating phototactic indices, for example, the time taken for the cells to move a certain distance, the number of moved cells, etc., are collected through microscopic observation, as described above.

If microalgae are used as single cell organism with mutation, the inventive method based on phototaxis may comprise the following steps.

In an embodiment, the method employing the system of the present invention may, for example, comprise the steps of: (a) culturing single cell organisms under a continuous light condition, and then culturing the single cell organisms under a dark condition; (b) introducing the pretreated single cell organisms into the cell inlet unit of the microfluidic photoreaction system; (c) irradiating the cell inlet unit with light so that phototaxis can be induced in the single cell organisms introduced in the cell inlet unit; (d) observing the single cell organisms, which move through the channel by phototaxis, through the measuring unit, thereby collecting phototactic indices; and (e) selecting the single cell organisms as mutant cells, if the phototactic indices differ from those of a control group. However, the method is not limited thereto. The pretreatment step may be optionally performed. The terms and description used in this method are as described above with respect to the method of the present invention.

EXAMPLES

Hereinafter, the present invention will be described in further detail with reference to examples. It will be obvious to a person having ordinary skill in the art that these examples are illustrative purposes only and are not to be construed to limit or change the scope of the present invention.

Example 1

Preparation of Mutant Strains

A strain used in this Example was *Chlamydomonas reinhardtii* species obtained from Professor Eon-Seon Jin (Hanyang University, Korea).

The strain was wild type strain JL428, and a random mutation was introduced into the wild-type strain by insertional mutation. Because it is generally known that strains having high chlorophyll a/b ratios are highly likely to have high photosynthesis efficiency (Anastasions Melis (2012) Vol. 158 930-945), strains having a chlorophyll a/b ratio higher than that of the wild type strain were selected and used to verify the effect of the inventive method.

The medium used in the culture of microalgae is a TAP medium containing the components shown in Table 1.

Example 2

Culture of Microalgae and Fabrication of Microfluidic System

A microfluidic system was fabricated by photolithography by spin-coating negative photoresist SU-8 50 on a silicon substrate, covering the coated photoresist with a designed mask and exposing the photoresist to UV light using a UV exposure system. Polymer PDMS (polydimethylsiloxane) and a curing agent were mixed at a ratio of 10:1 and coated on the SU-8 mold fabricated by photolithography. The fabricated PDMS microfluidic system was combined with slide glass by plasma treatment. The fabricated system is shown in FIG. 2*b*.

In order to select the optimal channel structure of the system, the motility of cells at various channel widths and shapes as shown in FIG. 2*a* was analyzed as described in Example 3 below. In brief, while the cell inlet unit containing cells was exposed to light from a green LED light source (540 nm), the number of cells that reached the opposite side (i.e., cell reaching unit) located at a certain distance from the cell inlet unit was measured in each of the systems, and the results of the measurement were compared. As a result, as shown in FIG. 3*b*, the movement of the cells by phototaxis was influenced by the width of a channel near the cell inlet unit in the microfluidic system. Thus, in order to minimize resistance to the movement of cells while facilitating the observation of individual cells in a measuring unit and statistical analysis, a system design comprising a channel having an inlet width of 4 mm and an outlet width of 100 μm as shown in FIG. 2*b* was selected and fabricated as described above.

Example 3

Analysis of Response of Microalgae to Light at Various Wavelengths of Light

In a pretreatment process for efficiently controlling the response and sensitivity of cells to light at constant levels, each of the *Chlamydomonas reinhardtii* wild type strain (JL428) and the mutant strains of Example 1 was seed-cultured in TAP agar medium. Specifically, each strain was cultured in TAP liquid medium under 24-hr light conditions at a light intensity of 40 μmol photon $m^{-2}s^{-1}$ and 23° C. for 2 days. After 2 days of culture, the cells reached the exponential phase, and the cells were diluted to a concentration of $7.5\times10^3$ cells $ml^{-1}$ and stored in a dark room for 1 hour.

Next, 40 μl of the cells stored in a dark room for 1 hour were placed in the cell inlet unit of FIG. 2*b*, and 40 μl of TAP medium was placed in the cell reaching unit, after which the movement of the microalgal cells by phototaxis was observed by an inverted optical microscope in the measuring unit.

In order to analyze the response of microalgae to light at various wavelengths of light, the cell concentration and conditions were maintained at constant levels as described above, and then the wavelength of LED light source used was changed. Under a total of five conditions, including green (540 nm), red (650 nm), blue (470 nm), white (full wavelength) and dark room conditions, the phototactic response of microalgae was analyzed.

Figure 3A:
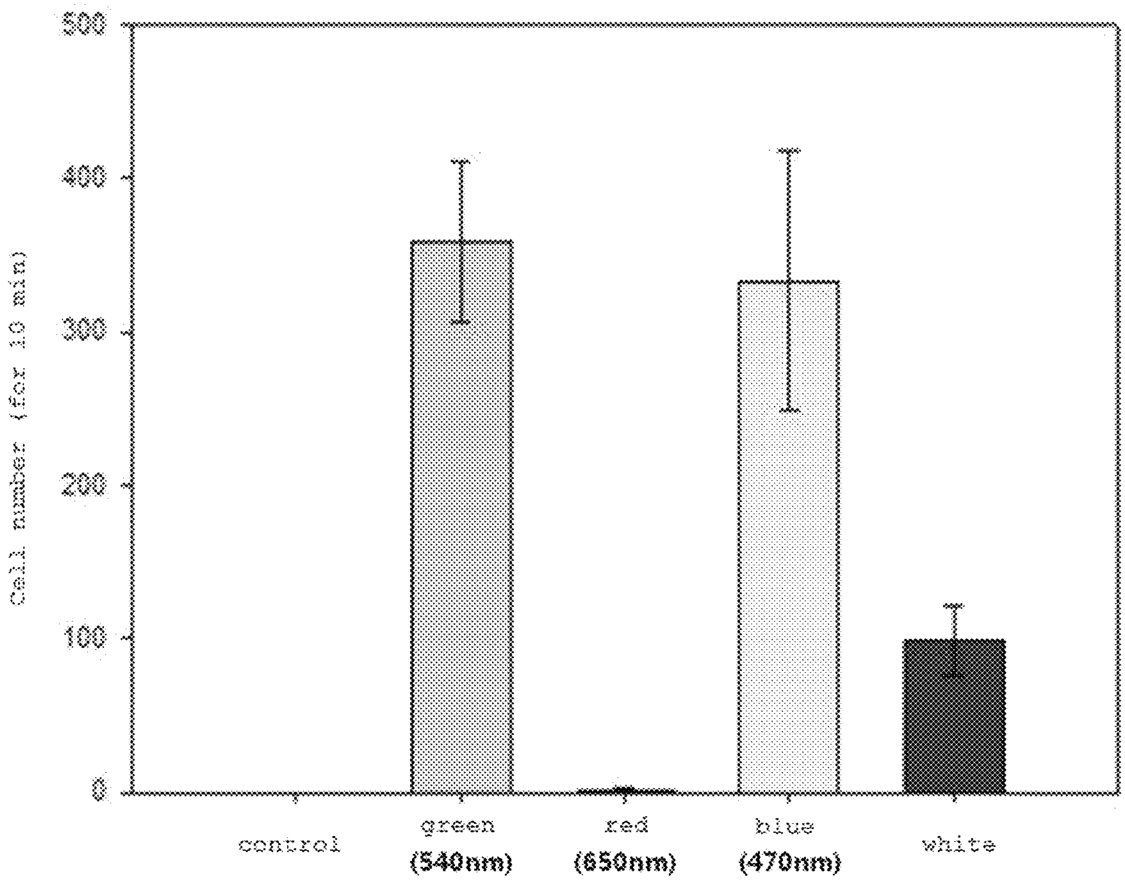
FIG. 3*a* is a graph showing the results of measuring phototactic response of the single cell organism to the light using LEDs at various wavelengths according to an embodiment of the present invention in order to determine the wavelength of the light source for efficient screening of single cell organisms based on phototaxis.
Figure 3B:
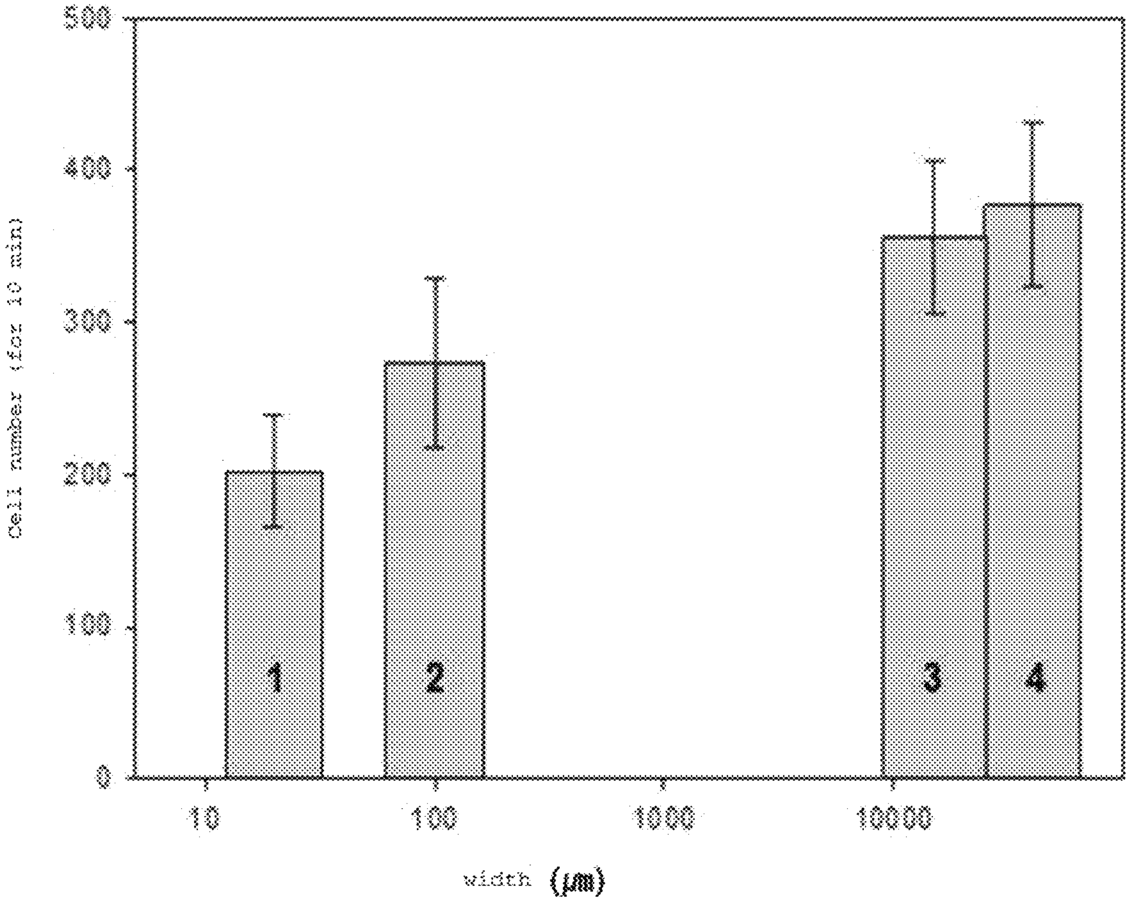
FIG. 3*b* is a graph showing the results of measuring the phototactic response of single cell organism to light using each of the microfluidic photoreaction systems shown in FIG. 2*a*. Numerals 1, 2, 3 and 4 on the graph of FIG. 3*b* correspond to the numerals described for the systems of FIG. 2*a*.

As a result, as shown in FIG. 3*a*, the microalgae showed a sensitive response at specific wavelengths. Specifically, the microalgae showed a great response at green (540 nm) and blue (470 nm) wavelengths, and showed no response to light at the red wavelength (650 nm). Based on such results, a green LED light source having a wavelength of 540 nm was used in the present invention.

Example 4

Light Response Pattern Analysis and Screening of Wild Type and Mutant Strains by Phototaxis The cell inlet unit was exposed to light from a green LED light source (540 nm) at a light intensity of 30 μmol photon $m^{-2}s^{-1}$, and the number of cells that reached the measuring unit was measured at 1-min intervals for 30 minutes. The results of the measurement are shown in FIG. 5. The number of cells that moved in response to light was analyzed as a function of time for each strain, and as a result, constant histograms were obtained. When the histograms of the mutant strains were compared with the histogram of the wild type strain, it was found that the peaks of the histograms of mutants 1, 2 and 3 were shifted to the left compared to that of the wild type strain. However, mutants 4 and 5 showed no significant difference from the wild type strain. In connection with the chlorophyll a/b ratio related indirectly to photosynthesis efficiency, strains having high chlorophyll a/b ratios are highly likely to have high photosynthesis efficiency. When the histograms obtained by phototaxis, it was shown that the number of cells that moved in response to light was larger in the strain having an increased chlorophyll a/b ratio than in the wild type strain and that the mutant strains showing no significant difference in the chlorophyll a/b ratio from the wild type strain showed little or no difference in the number of cells that moved by phototaxis. Thus, it can be seen that, when the patterns of the histograms of FIG. 5 are analyzed, the mutant strain having increased photosynthetic efficiency can be easily and efficiently identified by phototaxis.

Figure 6A:
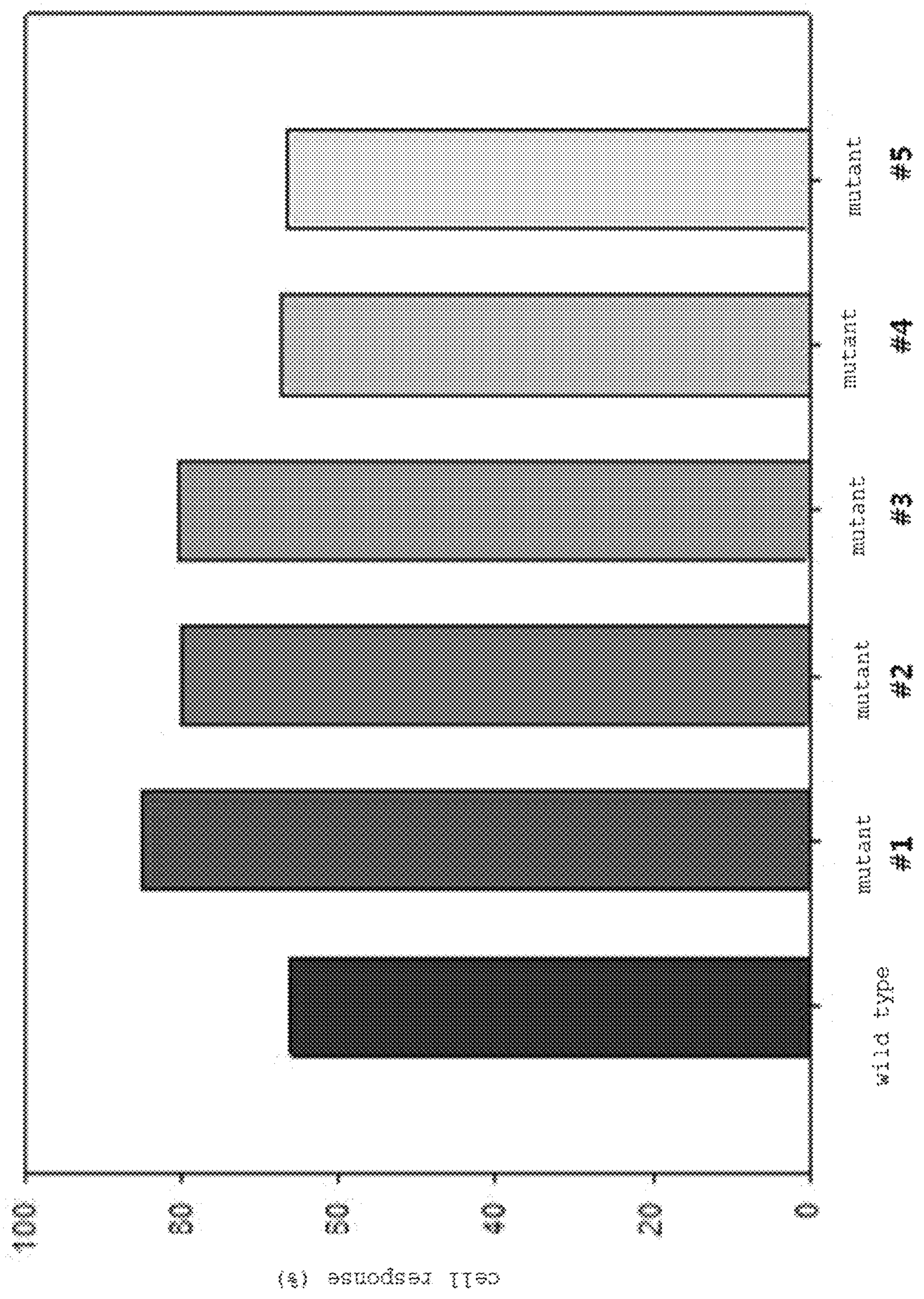
FIG. 6*a* is a graph showing the results of analyzing the light response based on the ratio of the number of cells showing a light response to the total number of cells in each of control and mutant strains.

FIG. 6*a* shows the results of measuring the percentage of the number of cells, which moved in response to light, relative to the total number of cells. When the responses of the mutant strains to light were compared with that of the wild type strain, it was found that 65% of total cells in the wild type strain showed a response to light, whereas 85% of total cells in mutant 1 moved in response to light, and about 80% of cells in mutants 2 and 3 showed a response to light. However, mutants 4 and 5 were similar to the wild type strain with respect to the percentage of cells that showed a response to light. Such results suggest that the mutant strains having increased photosynthetic efficiency resulting from an increase in the chlorophyll a/b ratio show a greater response to the same intensity of light compared to the wild type strain, and that the mutant strain having a chlorophyll a/b ratio similar to that of the wild type strain has photosynthetic efficiency similar to that of the wild type strain, and the response to this strain to light is similar to that of the wild type to the same intensity of light.

Figure 6B:
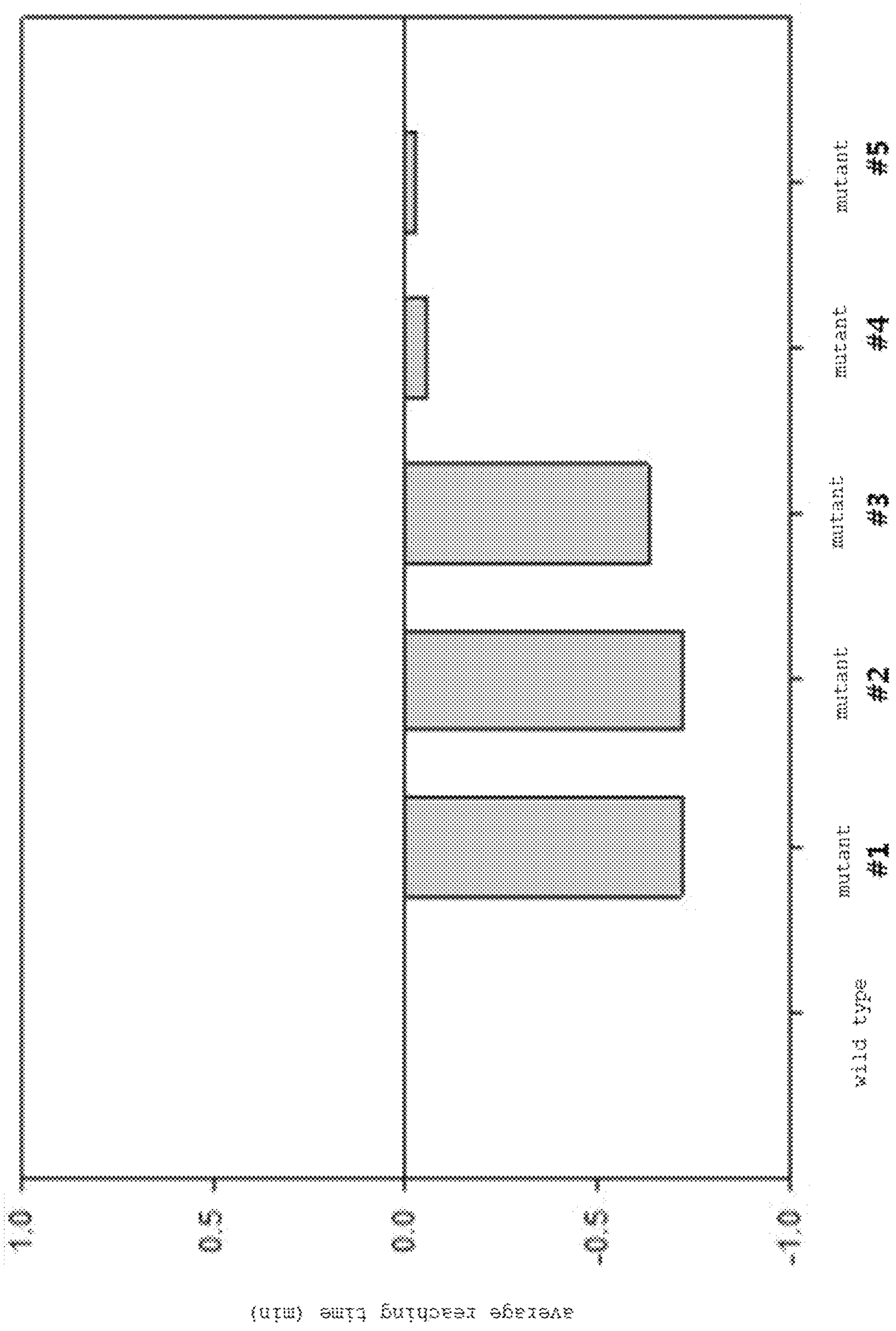
FIG. 6*b* is a graph showing the average reaching time taken for the control and mutant strains to move a certain distance (3 cm) by phototaxis, and shows a difference in light sensitivity between the mutant strains.

The sensitivities of the wild type and mutant strains to light can be comparatively analyzed by analyzing the variation in the average time taken for the cells to move in response to light. By doing so, it is possible to screen a strain having a specific response to light. As can be seen in FIG. 6*b*, the average reaching time was shorter in mutants 1, 2 and 3 than in the wild type, and the average reaching time of mutants 4 and 5 was not significantly shorter than that of the wild type. Such results suggest that the mutant strain having increased photosynthetic efficiency resulting from an increase in the chlorophyll a/b ratio is more sensitive to a certain intensity of light compared to the wild type strain, and this sensitivity is related to the movement speed of cells. Also, such results suggests that the strain having increased sensitivity to the same intensity of light moves in faster response to light, indicating that the time taken for the strain to move a certain distance (3 cm) is reduced. In addition, such results suggest that the strain having a chlorophyll a/b ratio similar to that of the wild type strain has sensitivity to a certain intensity of light, which is similar to that of the wild type strain, indicating that the time taken for the strain to move a certain distance is similar to that of the wild type strain.

Figure 4:
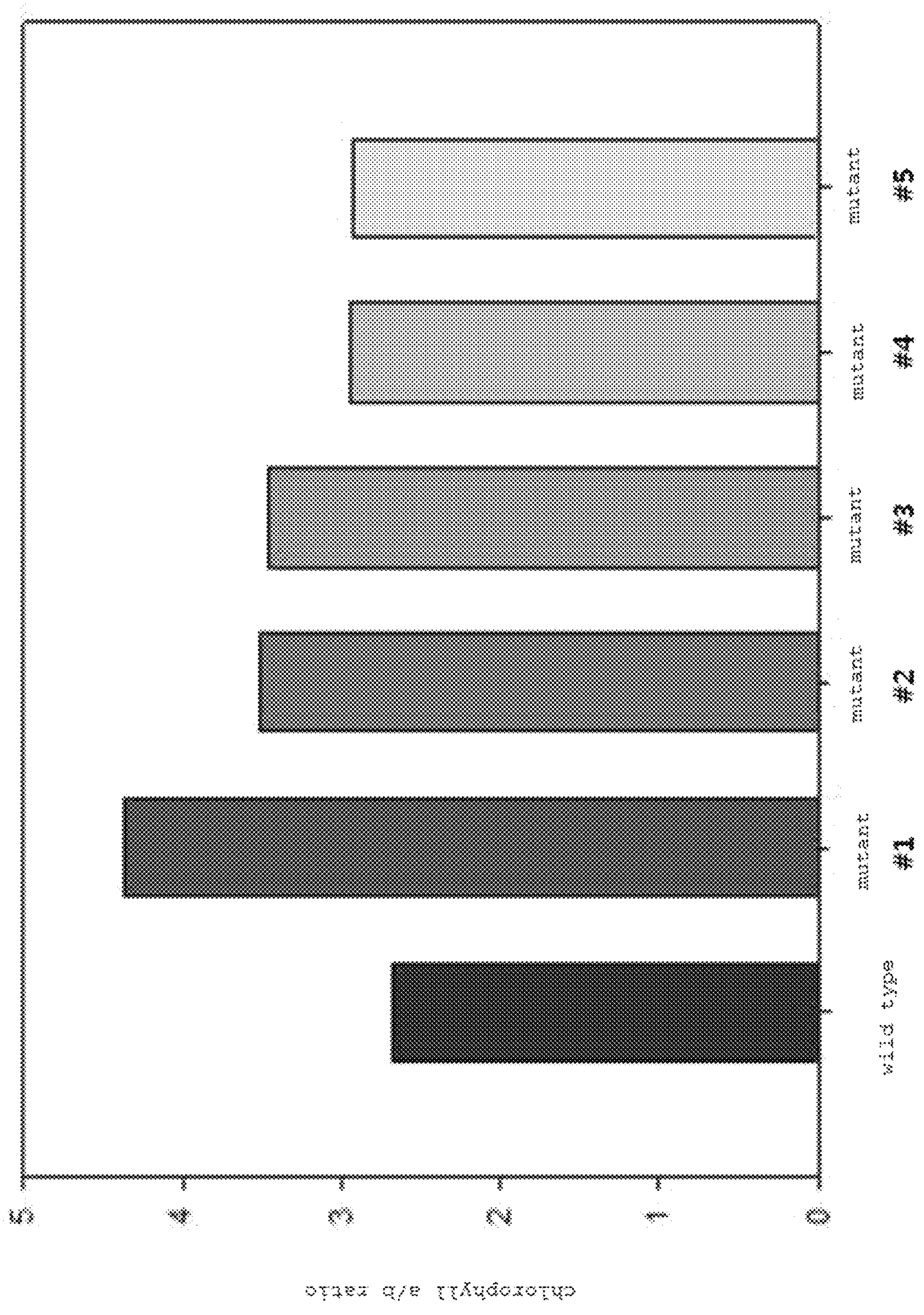
FIG. 4 is a graph showing the ratio of chlorophyll a to chlorophyll b (a/b ratio) in wild-type and 5 different mutant strains used in an embodiment of the present invention.
Figure 5:
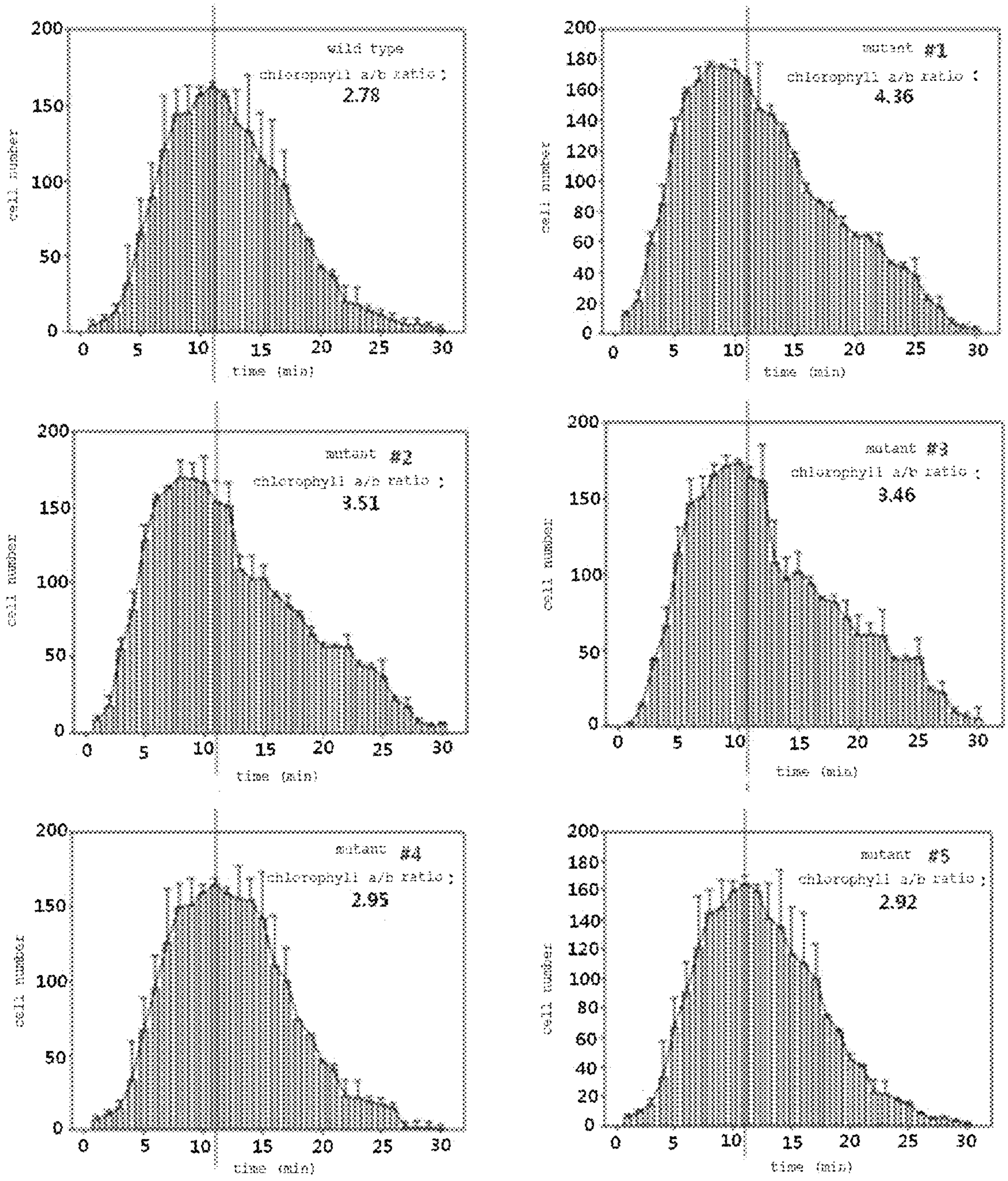
FIG. 5 depicts histograms showing the time-dependent distribution of the number of cells of microalgal strains showing a response to the light in a microfluidic photoreaction system according to an embodiment, and shows the light responses of a wild-type strain used as a control and mutant strains.

Meanwhile, as shown in FIGS. 5, 6*a* and 6*b*, the phototactic responses of the wild type and mutant strains to light showed a pattern significantly similar to that of the chlorophyll a/b ratios shown in FIG. 4. This indicates that various indices (peaks of histograms, average movement time, the ratio of cells that responded to light, etc.) obtained by statistical analysis for the light response of each of the strains used in the present invention may have a connection not only with a phototactic response and sensitivity to light, but also changes in photosynthetic mechanisms such as chlorophylls, which are caused by mutation.

Thus, from strains primarily screened using the analysis method for the phototaxis of microalgae in the microfluidic system used in the present invention, a strain having increased photosynthetic efficiency can be more efficiently screened.

Example 5

Analysis of Photosynthetic Indices of Screened Mutant Strains

In this Example, the photosynthetic efficiencies of the mutant strains screened based on phototaxis were measured. As indices, NPQ and qP were used. NPQ is energy that dissipates without being used for photosynthesis among light energy that received for photosynthesis, and lower NPQ values indicate higher photosynthetic efficiency. qP means energy that is used for photosynthesis, and higher qP values indicate higher photosynthetic efficiency.

5-1: Analysis of Correlation Between Chlorophyll a/b Ratio of Screened Strain and each of NPQ and qP The correlation between the chlorophyll a/b ratio of the screened strain and each of NPQ and qP was analyzed in the following manner. Chlorophylls were measured by a known method (Hartumut K. Lichtenthaler and Claus Buschmann (2001) F4.3.1-F4.3.8) based on absorbance measurement.

In brief, microalgal cells were cultured in a flask at a light intensity of 40 μmol photon $m^{-2}s^{-1}$ for 3 days. Next, when the cells reached the exponential phase, chlorophyll measurement was performed. Specifically, the flask was well shaken, and 1 ml of the flask content was transferred into a 1.5 ml tube and centrifuged at 15,000 rpm for 1 minute. After centrifugation, the supernatant was removed, and 1 ml of methanol was added to the cell pellet which was then vortexed to extract chlorophyll. Thereafter, chlorophylls a and b were measured using the following equations, thereby measuring the chlorophyll a/b ratio.

$$\text{Chl } a\ (g/ml)=16.72\times A665.2-9.16\times A652.4$$

$$\text{Chl } b\ (g/ml)=16.72\times A652.4-15.28\times A665.2$$

$$\text{Chl } a/b=\text{Chl } a\div\text{Chl } b$$

NPQ and qP were measured using an imaging-PAM chlorophyll fluorometer (Heinz Walz GmbH, Germany) after the strain was cultured in TAP agar medium at 23° C.

Next, the data obtained by analysis in Examples 3 to 5, that is, the average movement time, the cell ratio of the cell colonies that reached per unit time, the chlorophyll a/b ratio, NPQ and qP, were analyzed.

Figure 7A:
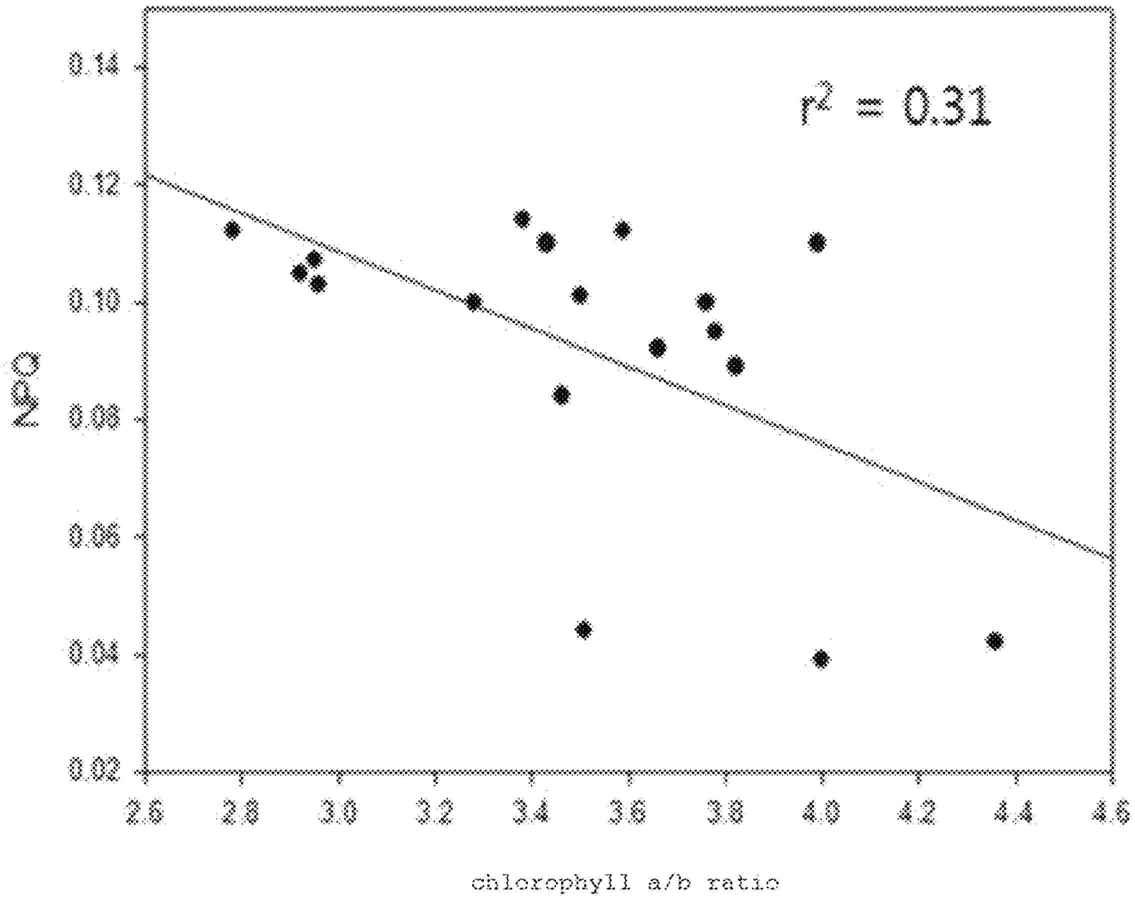
FIG. 7*a* is a graph showing the correlation between the chlorophyll a/b ratio and NPQ. As the chlorophyll a/b ratio increased, the NPQ (non-photochemical quenching) value decreased, indicating that the photosynthetic efficiency was high.
Figure 7B:
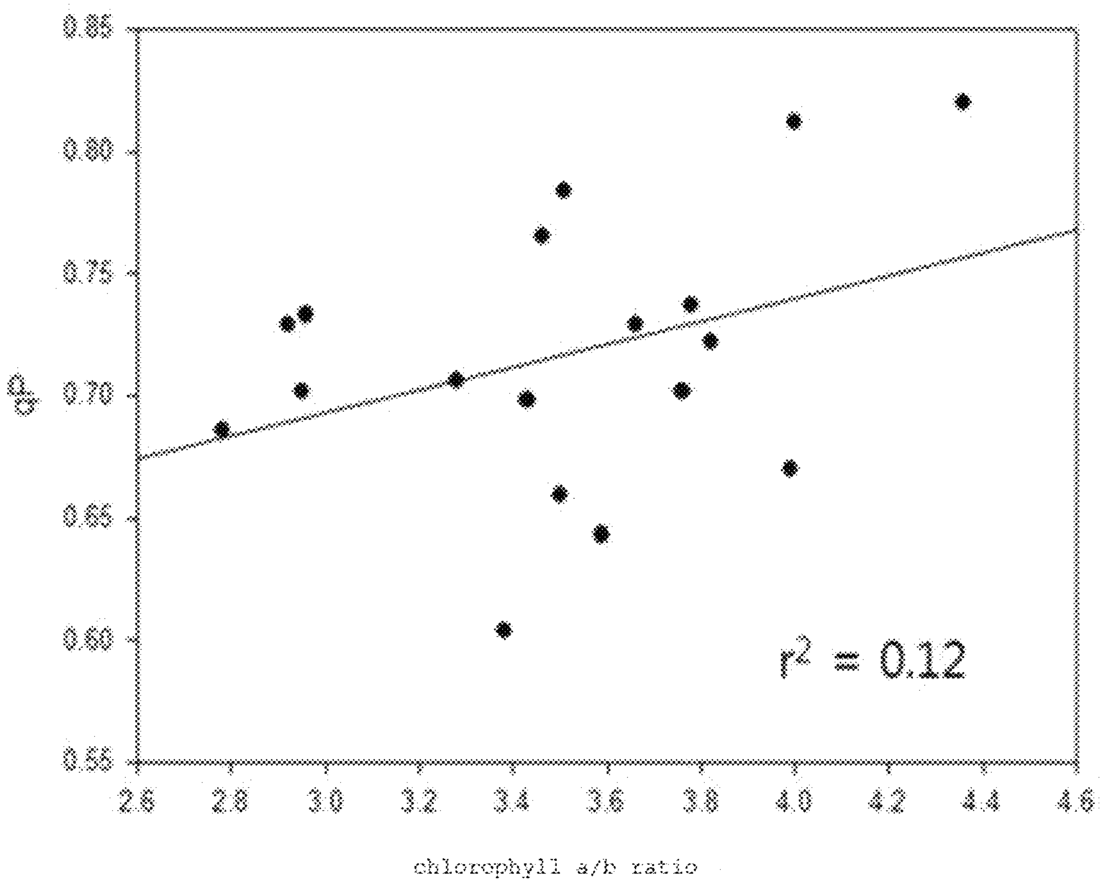
FIG. 7*b* is a graph showing the correlation between the chlorophyll a/b ratio and qP (photochemical quenching). As the chlorophyll a/b ratio increased, the qP value increased, indicating that the photosynthetic efficiency was high.

The results of the analysis are shown in FIGS. 7*a* and 7*b*. As can be seen therein, as the chlorophyll a/b ratio increased, the NPQ value decreased and the qP value increased, indicating that the photosynthetic efficiency was high.

5-2: Analysis of Correlation Between Average Reaching Time of Screened Strain and NPQ The correlation between the average reaching time among the phototactic indices obtained for each strain as described in Example 4 and the indices for measuring photosynthetic efficiency as described in Example 5 was analyzed.

The results of the analysis are shown in FIGS. 8*a* and 8*b*. As can be seen therein, as the r2 value that indicates the correlation between the two indices is closer to 1, the correlation is higher. Thus, the results indicate that the indices obtained by phototaxis according to the present invention is more effective in screening a mutant strain having increased photosynthetic efficiency, compared to the chlorophyll a/b ratio used in the prior art.

5-3: Analysis of Correlation Between Ratio of Number of Moved Cells of Screened Strain to that of Wild Type Strain and NPQ The correlation between the ratio of the number of moved cells in the mutant strain to that in the wild type strain, among the phototactic indices obtained for each strain as described in Example 4, and the index for measuring photosynthetic efficiency as described in Example 5, was analyzed.

The results of the analysis are shown in FIG. 9. As can be seen therein, the ratio of the number of moved cells in the mutant strain to that in the wild type strain was 1 or more, indicating that a larger number of cells in the mutant strain compared to that in the wild type strain moved. This suggests that the mutant strain has a high response and sensitivity to light. Also, the ratio of the number of moved cells in this mutant strain showed a low correlation with the NPQ value, indicating that this strain has increased photosynthetic efficiency. Thus, such results indicate that, when the inventive method based on phototaxis is used, it is possible to screen a strain having increased photosynthetic efficiency.

INDUSTRIAL APPLICABILITY

As described above, according to the present invention, improved single cell organisms can be effectively screened based on phototaxis using a microfluidic system. Specifically, easy monitoring at the cellular level is possible, and a mutant strain having an increased response and/or sensitivity to light can be easily and rapidly screened by various analyses, including statistical analysis of collected results. Thus, the present invention can be effectively used to investigate the correlation between phototaxis and photoconversion efficiency and to screen a single cell organism having increased photoconversion efficiency.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method of screening to identify a single cell organism having a mutation that affects its phototaxis, the method comprising the steps of:

(a) obtaining a collection of single cell organisms, wherein one or more of the single cell organisms may have a mutation that affects its phototaxis;

(b) pretreating the collection of single cell organisms by culturing each organism under continuous light, wherein the light has a wavelength of 540-600 nm or 430-500 nm and an intensity of 20-50 μmol of photons $m^{-2}s^{-1}$, and then culturing each organism in the dark;

(c) irradiating the collection of single cell organisms with light to induce phototaxis;

(d) calculating the phototactic indices of each culture of the single cell organisms; and (e) selecting a single cell organism as the desired single cell organism having a mutation in phototactic ability, if the phototactic indices of the selected single cell organism differ from those of a control group of phototactically normal single cell organisms.

2. The method of claim 1, wherein the single cell organism is cultured to the exponential phase of the cell growth cycle in the pretreatment step.

3. The method of claim 1, wherein the single cell organism is derived from either single colonies or multiple colonies.

4. The method of claim 1, wherein the phototaxis is either positive phototaxis or negative phototaxis.

5. The method of claim 4, wherein the phototaxis is negative phototaxis that is induced by irradiating light having a wavelength of 540-600 nm or 430-500 nm and an intensity of 20-50 μmol of photons $m^{-2}S^{-1}$.

6. The method of claim 1, wherein the phototactic indices of the single cell organisms are calculated through the measurement of at least one of the light response and the light sensitivity.

7. The method of claim 1, wherein the desired single cell organism having the mutation has one or more improved indices of photosynthesis, including changes in photosynthetic mechanisms including photosynthetic pigments, photosynthesis efficiency and photoconversion efficiency, and growth rate in comparison with the control group.

8. The method of claim 1, wherein the phototactic indices include: (i) the ratio of the number of single cell organisms that moved per unit time in response to light to the total number of single cell organisms used; (ii) histogram peak analysis based on the distribution of the number of single cell organisms that moved per unit time; or (iii) the average time taken for single cell organisms to move a unit distance, the speed of the movement, or the variation in their position.

9. The method of claim 1, further comprising measuring the phototactic indices for the screened single cell organisms.

10. The method of claim 9, wherein the phototactic indices include changes in photosynthetic mechanisms including photosynthetic pigments, photosynthesis efficiency and photoconversion efficiency.

11. The method of claim 1, wherein the single cell organisms are microalgae.

12. The method of claim 11, wherein the microalgae are green algae, diatoms, red algae, flagellates, light green algae, brown flagellates, yellow-green algae, dinoflagellates, or blue-green algae.

13. The method of claim 12, wherein the Green algae are *Chlamydomonas* spp.

14. The method of claim 13, wherein the *Chlamydomonas* sp. is *Chlamydomonas reinhardtii*.

* * * * *

UNITED STATES PATENT AND TRADEMARK OFFICE

CERTIFICATE OF CORRECTION

PATENT NO. : 9,650,659 B2
APPLICATION NO. : 14/760607
DATED : May 16, 2017
INVENTOR(S) : Sang Jun Sim et al.

It is certified that error appears in the above-identified patent and that said Letters Patent is hereby corrected as shown below:

In the Specification

Column 13, Line 46: "Chl *b (g/ml)* = 16.72×*A*652.4 — 15.28×*A*665.2" should be
--Chl *b (g/ml)* = 34.09×*A*652.4 — 15.28×*A*665.2--.

Signed and Sealed this
Twentieth Day of June, 2017

Joseph Matal

*Performing the Functions and Duties of the*
*Under Secretary of Commerce for Intellectual Property and*
*Director of the United States Patent and Trademark Office*